United States Patent [19]
Hubbard

[11] Patent Number: 5,595,181
[45] Date of Patent: Jan. 21, 1997

[54] SYSTEM FOR PROVIDING CARDIAC OUTPUT AND SHUNT QUANTITATION

[76] Inventor: A. Robert Hubbard, 632 E. Center St. #37, Rochester, Minn. 55938

[21] Appl. No.: 217,243

[22] Filed: Mar. 24, 1994

[51] Int. Cl.⁶ ........................................ A61B 5/00
[52] U.S. Cl. ................. 128/692; 128/713; 128/668
[58] Field of Search ............................ 126/668, 672–675, 126/691–694, 713, 736

[56] References Cited

U.S. PATENT DOCUMENTS

| | | | |
|---|---|---|---|
| 3,726,269 | 4/1973 | Webster, Jr. | 128/2.05 F |
| 4,105,022 | 8/1978 | Antoshkiw et al. | 128/2.05 F |
| 4,212,298 | 7/1980 | Gezari | 128/692 |
| 4,476,877 | 10/1984 | Barker | 128/692 |
| 4,502,488 | 3/1985 | Degironimo et al. | 128/713 |
| 4,621,646 | 11/1986 | Bryant | 128/692 |
| 4,676,252 | 6/1987 | Trautman et al. | 128/671 |
| 4,696,304 | 9/1987 | Chin | 128/673 |
| 4,796,640 | 1/1989 | Webler | 128/736 |
| 4,841,981 | 6/1989 | Tanabe et al. | 128/692 |
| 4,901,734 | 2/1990 | Griffin et al. | 128/692 |
| 5,009,234 | 4/1991 | Alt | 128/736 |
| 5,271,410 | 12/1993 | Wolzinger et al. | 128/692 |

OTHER PUBLICATIONS

Fred Morady, MD, Bruce H. Brundage, MD, and Harris J. Gelberg, MD, *Rapid Method for Determination of Shunt Ratio Using a Thermodilution Technique*, American Heart Journal, 106:369–373, Aug. 1983.

L. David Hillis, MD, Brian G. Firth, MD, DPhil, and Michael D. Winniford, MD, *Analysis of Factors Affecting the Variability of Fick Versus Indicator Dilution Measurements of Cardiac Output*, American Journal of Cardiology, 56:764–768, 1985.

Horacio Pomes Iparraguirre, MD, Rodolfo Giniger, MD, Eduardo R. Malvino, MD, Victor A. Garber, MD, Miguel A. Jorge, MD, Policlinica Bancaria, *Computerized Fick Cardiac Output vs. Thermodilution*, Critical Care Medicine, pp. 624–625, Jun. 1987.

Spencer H. Kubo, MD, J. E. B. Burchenal, AB, and Robert J. Cody, MD, *Comparison of Direct Fick and Thermodilution Cardiac Output Techniques at High Flow Rates*, American Journal of Cardiology, (Brief Reports) pp. 384–386, Feb. 1987.

Robert M. Sade, MD, Abdel Aziz Richi, MD, and James P. Dearing, BS, *Calculation of Systemic Blood Flow with Pulmonary Artery Thermistor Probe*, J. Thorac Cardiovasc Surg 78:576–578, 1979.

*Thermodilution and Cardiac Output*, Chapter 1, pp. 1–2.

*Cardiac Output*, Medical Electronics, pp. 126–128, Apr. 1986.

*Thermodilution Technique*, Cardiac Output/Cardiac Catheterization, pp. 77–82.

Gary F. Maruschak, RCPT, Alan M. Potter, BS, James F. Schuable, MD, and Mark C. Rogers, MD, *Overestimation of Pediatric Cardiac Output By Thermal Indicator Loss*, Circulation, vol. 65, No. 2, pp. 380–383, Feb. 1982.

(List continued on next page.)

*Primary Examiner*—Angela D. Sykes
*Assistant Examiner*—Robert L. Nasser, Jr.
*Attorney, Agent, or Firm*—Westman, Champlin & Kelly, P.A.

[57] ABSTRACT

A system for providing cardiac output from a patient includes a catheter having a proximal end, a distal end, a lumen between the proximal and distal ends, and an injection port communicating with the lumen. A first temperature sensor is placed in a blood vessel exiting a first heart ventricle of the patient. A second temperature sensor is placed proximate the injection port. A cardiac output test is performed injecting a medium (or bolus) having contrasting temperature into a first heart chamber of the patient. The injectate temperature is sensed by the second temperature sensor. Blood temperature is sensed by the first temperature sensor as blood carries the medium through the blood vessel. A set of curve data, representative of the sensed blood temperature as a function of time, is stored. The cardiac output test is repeated until a first plurality of sets of curve data are stored. At least one of the first plurality of sets of curve data are displayed.

19 Claims, 6 Drawing Sheets

OTHER PUBLICATIONS

Elaine Kiess Daily, RN, BS, RCVT, and Joan Mersch, RN, MS, *Thermodilution Cardiac Outputs Using Room and Ice Temperature Injectate: Comparison With the Fick Method,* Heart & Lung, vol. 16, No. 3, pp. 294–300, May 1987.

Marlene Barcelona, RN, Lilian Patague, RN, Magda Bunoy, RN, Marianito Gloriani, MD, Berdie Justice, RN, and Lucianne Robinson, RN, *Cardiac Output Determination By the Thermodilution Method: Comparison of Ice–Temperature Injectate Versus Room–Temperature Injectate Contained in Prefilled Syringes or a Closed Injectate Delivery System,* Heart & Lung, vol. 14, No. 3, pp. 232–235, May 1985.

Loren D. Nelson, MD, and Hans B. Anderson, RRT, *Patient Selection for Iced Versus Room Temperature Injectate for Thermodilution Cardiac Output Determinations,* Critical Care Medicine, vol. 13, No. 3, pp. 182–184, Mar. 1985.

Polly E. Gardner, RN, MN, Lise A. Monat, RN, MN, and Susan L. Woods, RN, MN, *Clinical Studies: Critical Care Nursing Strategies—Accuracy of the Closed Injectate Delivery System in Measuring Thermodilution Cardiac Output,* Heart & Lung, vol. 16, No. 5, pp. 552–561, Sep. 1987.

Ricardo G. Cigarroa, MD, Richard A. Lange, MD, and L. David Hillis, MD, *Oximetric Quantitation of Intracardiac Left–To–Right Shunting: Limitations of the Qp/Qs Ratio,* Apr. 1989 (one sheet).

Gunnel Hedvall, MD, *The Applicability of the Thermodilution Method for Determination of Pulmonary Blood Flow and Pulmonary Vascular Resistance in Infants and Children with Ventricular Septal Defects,* Scand. J. Clin. Lab. Invest. 38, pp. 581–585, 1978.

B. Braun, *A Revolution Thermodilution—The Nove Dualtherm,* Nova Medical Specialties, Inc., pp. 1–4.

Bruce S. Alpert and Casimir Eubig, *Thermodilution Qp/Qs: An Indicator Dilution Method,* Pediatric Cardiology, 4:13–17, 1983.

SYSTEM FOR PROVIDING CARDIAC OUTPUT AND SHUNT QUANTITATION

BACKGROUND OF THE INVENTION

The present invention relates to a cardiac monitoring device. More particularly, the present invention relates to a system for monitoring and displaying cardiac output and shunt quantitation in a patient.

One of the most important parameters of the circulatory system which is monitored and observed in patients is cardiac output. Cardiac output is indicative of blood flow to all tissues of the body and may be expressed as a product of heart rate and volume of blood pumped per beat of the heart. Cardiac output is typically measured in liters per minute.

Thermodilution has been used to determine cardiac output in patients. Typically, a thermodilution catheter is inserted, usually via a femoral vein, into the heart. The thermodilution catheter has a thermistor at its distal end which is inserted commonly into the pulmonary artery. Proximal of the thermistor is an injection port on the thermodilution catheter which is inserted in the venae cavae, or in the right atrium of the heart. A small, known amount of thermal indicator is introduced through the injection port in the thermodilution catheter into the right atrium of the heart. The thermal indicator is then carried by the blood through the heart to the pulmonary artery.

The injectate is commonly a 5% dextrose solution in water which is immersed in an ice bath external to the patient. The injectate temperature is therefore assumed to be approximately 0° C. when it is injected into the atrium. As the thermal indicator mixes with surrounding blood in the heart, it cools the temperature of the blood before the blood is pumped out of the heart and passes the thermistor. The thermistor measures the decrease in blood temperature as the blood flows past the thermistor in the pulmonary artery. This information is monitored by a cardiac output computer which plots the decrease in blood temperature over time. The area under the time-temperature curve is inversely proportional to the flow rate (mass per unit time) of blood. The flow rate corresponds to cardiac output in that the temperature decrease in the blood will be greater, and will extend over a longer time period in slowly flowing blood than in blood which is flowing more quickly through the pulmonary artery. The thermodilution computer thus integrates the area under the time-temperature curve and uses this area to determine cardiac output.

In injecting the injectate into the patient, the physician, or other administering person, typically removes the injectate from the ice bath, and transfers it from a syringe to the thermodilution catheter where it flows along the catheter, (which is now inserted in the patients body) until it finally reaches the injection port. During this time, the injectate naturally warms from its original 0° C. temperature. Thus, cardiac output has commonly been determined using the area under the time-temperature curve and an equation which includes a correction factor that is the estimated increase in injectate temperature which will occur during injection. However, this temperature increase is only an estimation and can vary significantly from the estimated value, thus introducing significant errors into the cardiac output calculation.

Further, in many prior systems, it was common to reject or discard the results from the initial cardiac output test or subsequent tests since the thermal correction factor which was intended to compensate for warming of the thermal indicator during the injection process was inaccurate during the diagnostic procedure. The correction factor was not accurate because, during the injection, the catheter, at body temperature, warms the injectate significantly. Thus, the normal correction factor would not apply to the results of the cardiac output test, and these results were discarded. This was quite time inefficient.

In addition, in prior systems the physician is required to estimate the exact moment at which the injection takes place and typically marks that moment by manually actuating a switch, or other device which is input to the thermodilution computer, to trigger the beginning of the cardiac output test. Requiring the physician, or other administering person, to inject the injectate and also manually actuate a switch to trigger the beginning of the cardiac output test sequence is cumbersome and susceptible of errors. This introduces additional inaccuracies into the cardiac output calculation.

Also, in prior systems, a hot stylus has been used to plot the time-temperature curve on a strip chart recorder. The thermodilution computer then prints out the cardiac output value. In order to assess progress, the physician must compare printouts of the time-temperature curve, and the cardiac output values printed out by the computer. This is a time consuming and inaccurate process.

Another cardial problem has also been the subject of much research. Septal defects are, in essence, holes in the septum of the heart which allow communication between two heart chambers. For example, ventricular septal defects (the most common congenital heart defects) provide a hole in the septum of the heart separating the ventricles. Thus, the ventricles are in fluid communication with one another. Such a condition is very undesirable.

Septal defects can be diagnosed using the ratio of the quantity of pulmonary blood flow to the quantity of systemic blood flow ($Q_p/Q_s$). In normal individuals, these two blood flows are equal and the ratio is 1:1. However, in patients with atrial or ventricular septal defects, blood flow occurs from the left heart chamber, through the defect, to the right heart chamber. This shunt flow occurs because the resistance to systemic blood flow is significantly higher than the resistance to pulmonary blood flow.

The shunt flow results in increased blood flow to the lungs, and possibly decreased blood flow to the remainder of the body tissues. Extra flow through the lungs leads to damage to the small blood vessels within the lungs if the defect is not closed quickly enough. This damage is permanent since the lungs do not have the capability to repair these small blood vessels. In addition to permanent damage to the blood vessels in the lungs, such defects have deleterious effects on the remaining body tissue since systemic blood flow can be reduced. If it is reduced, the blood provides less oxygen to the body tissue.

It is generally recognized that the need to surgically close an atrial defect is dictated by a $Q_p/Q_s$ ratio in excess of approximately 1.5:1. The need to surgically close a ventricular defect arises with a $Q_p/Q_s$ ratio in excess of 2:1 if such a defect is diagnosed in a child over two years of age. The need for surgery at earlier ages is highly dependent upon the $Q_p/Q_s$ ratio determined for the individual patient.

Determining the $Q_p/Q_s$ ratio is also referred to as shunt quantitation because it allows a trained physician to determine the extent, or quantity, of the septal defect. Previous methods have been used to perform shunt quantitation. The first is known as the Fick technique (also referred to as oxygen saturation measurement) which determines the $Q_p/Q_s$ ratio from directly determining blood oxygen content in central veins, heart chambers, and the arteries which supply both the lungs and the body. The second previous technique is known as the dye indicator dilution technique. This technique commonly includes the use of indocyanine green dye injected into the right heart chamber and sampled from a body artery. A third technique used in determining shunt quantitation is referred to as radionuclide angiography (also referred to as radioisotope indicator dilution technique). This method involves introducing radioactive material into a vein and scanning for radioactivity within the lungs.

All three techniques have significant disadvantages. The first two techniques require the removal of blood samples from an artery. In the third technique, the patient is subjected to undesirable levels of radiation.

A final technique for determining shunt quantitation is Doppler echocardiography. In such systems, Doppler imaging is used in an attempt to obtain both cardiac output and shunt quantitation values. However, Doppler echocardiography has inherent inaccuracies when trying to quantify blood flow through the defect.

SUMMARY OF THE INVENTION

The present invention is a system for determining cardiac output from a patient. A catheter is provided which has a proximal end, a distal end, a channel between the proximal and distal ends, and an injection port communicating with the channel. A first temperature sensor is placed in a blood vessel exiting the affected chamber of a patient's heart. A second temperature sensor is placed proximate the injection port. A cardiac output test is conducted by injecting injectate into a right atrium of the patient. The temperature of the injectate is sensed by the second temperature sensor. The blood temperature is sensed by the first temperature sensor as the blood carries the injectate from the heart through the blood vessel. A set of curve data, representative of the sensed blood temperature as a function of time, is stored, and the cardiac output test is repeated until a plurality of sets of curve data are stored. At least one of the sets of curve data are then displayed for inspection.

In one preferred embodiment, the present system is also used to determine a ratio of pulmonary blood flow to systemic blood flow ($Q_p/Q_s$) based on the set of curve data. This ratio is then provided to the physician so that the patient may be treated based on the $Q_p/Q_s$ ratio.

DETAILED DESCRIPTION OF THE PREFERRED EMBODIMENTS

Figure 1:
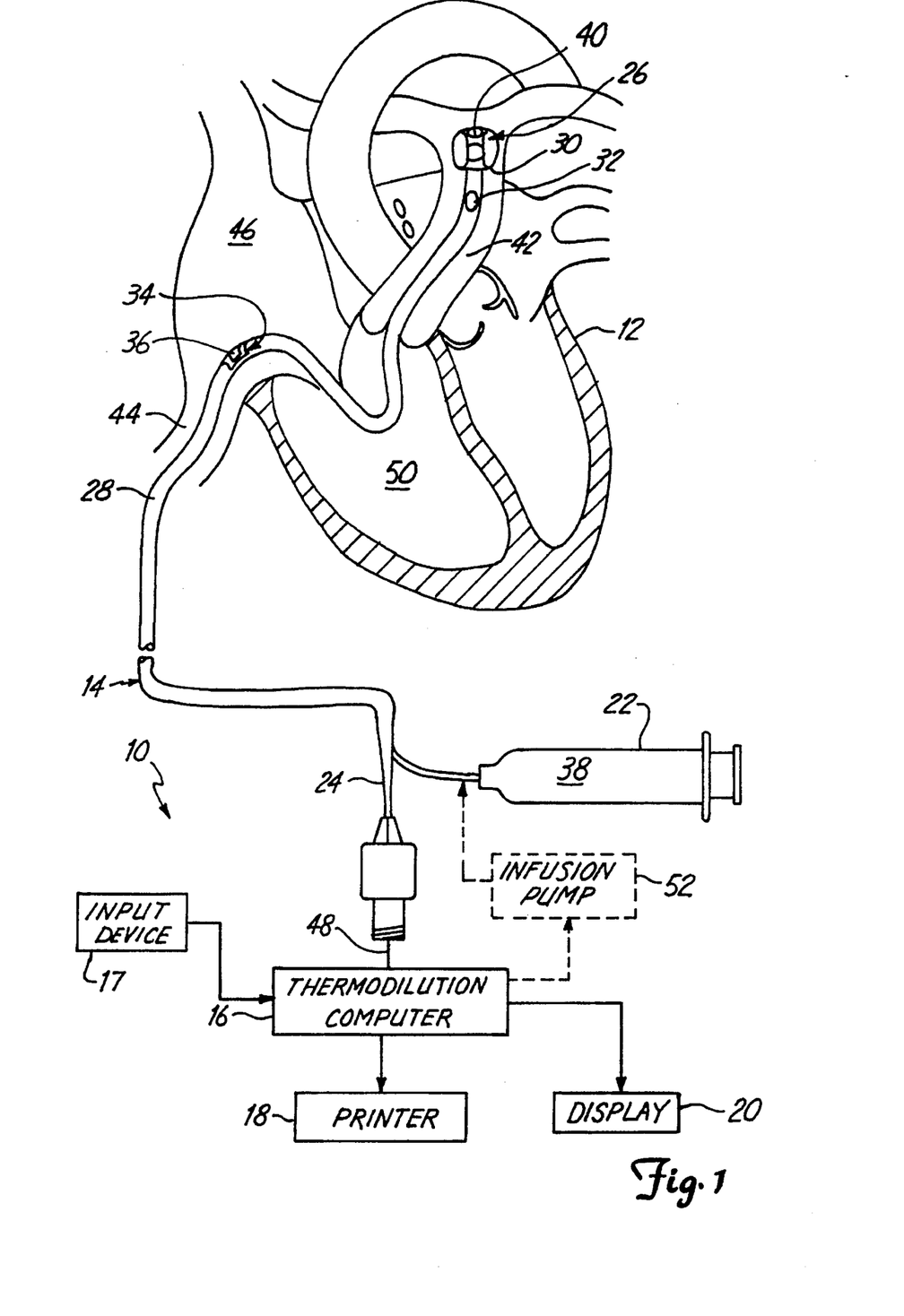
FIG. 1 illustrates the present system in use.

FIG. 1 shows cardiac output system 10 deployed in a heart 12. Cardiac output system 10 includes thermodilution catheter 14, thermodilution computer 16, input device 17, printer 18, display 20 and syringe 22. Catheter 14 includes a proximal end 24 and a distal end 26. Catheter 14 has a tube 28 which runs generally from the proximal end 24 to the distal end 26. Tube 28 defines a number of channels or lumens (which will be described in greater detail with respect to FIG. 6 and 7) which run generally between proximal end 24 and distal end 26. Catheter 14 also includes a balloon 30 mounted at the distal end 26, and a distal thermistor 32 mounted just proximal of balloon 30. In addition, catheter 14 includes an injection port 34 located proximal of distal thermistor 32 and in communication with an injectate lumen in tube 28. A portion of tube 28 is cut away to show an injection thermistor 36, located just proximal of injection port 34 in the injectable lumen in tube 28. In the preferred embodiment, thermistor 36 is mounted approximately 1 centimeter proximal of the injection port 34. Also, in the preferred embodiment, distal end 26 of catheter 14 includes a radiopaque band 40 used during insertion of catheter 14 in a known manner.

Syringe 22 communicates with the injectate lumen in tube 28 and holds a thermal indicator solution 38. Thermal indicator 38 is preferably a 5% dextrose solution in water which has a temperature that contrasts body temperature. Preferably, thermal indicator 38 has been immersed in an ice bath so that it is cooled to approximately 0° C.

Prior to initiating any cardiac output test, an operator provides thermodilution computer 16 with any number of desirable input parameters, such as patient identification information, patient age, patient weight, or any other desired statistics. The operator provides the thermodilution computer 16 with this information via input device 17 which, in the preferred embodiment, is a membrane keypad, a keyboard, or another suitable input device. Catheter 14 is inserted, through an appropriate vein or artery, so that its distal end 26 is positioned to locate distal thermistor 32 in pulmonary artery 42. In addition, catheter 14 is preferably positioned such that injection port 34 is located in the vena cava 44 or right atrium 46 of heart 12. Thermistors 32 and 36 are connected to thermodilution computer 16 by conductors 48 which run through a conductor lumen defined by tube 28.

In operation, the attending physician, or other attending person, injects thermal indicator 38 from syringe 22 into the injection lumen in catheter 14. Thermal indicator 38 travels along the injection lumen to injection port 34 where it enters right atrium 46 of heart 12. Since injection thermistor 36 is located in the injection lumen, thermal indicator 38 contacts thermistor 36 just prior to being injected through injection port 34. Thermistor 36 thus sends a signal to thermodilution computer 16 indicative of the precise temperature of the thermal indicator 38 as it is injected into heart 12. Upon receiving the signal from thermistor 36, thermodilution computer 16 is triggered to begin a cardiac output test. Thus, thermodilution computer 16 does not begin the test until the precise moment that thermal indicator 38 is injected into heart 12.

Once thermal indicator 38 is injected into right atrium 46, it mixes with blood in right atrium 46 and is pumped, through normal heart pumping action, into right ventricle 50. The thermal indicator 38 continues mixing with the blood in right ventricle 50 and is pumped out of right ventricle 50 into pulmonary artery 42. As the blood mixes with thermal indicator 38, the blood cools.

Just prior to the injection of thermal indicator 38, distal thermistor 32 provides thermal dilution computer 16 with a signal indicative of the temperature of the blood in pulmonary artery 42 before it is cooled by the thermal indicator 38. When the cooled blood, cooled from its mixture with thermal indicator 38, passes distal thermistor 32 in the pulmonary artery 42, thermistor 32 provides thermodilution computer 16 with a continuous signal which indicates that the thermal indicator 38 has reached thermistor 32 and is being pumped out of the pulmonary artery 42. After the thermal indicator 38 is pumped from right ventricle 50 through pulmonary artery 42, it circulates through the vascular system and the blood begins to rewarm. This is detected by thermistor 32. By recording the initial temperature reading from thermistor 36, and the temperature readings from distal thermistor 32 over time, thermodilution computer 16 obtains data necessary to plot a time-temperature curve used in calculating cardiac output. This curve, and the subsequently calculated cardiac output value, is then provided by thermodilution computer 16 to printer 18 and display 20 for use by the physician.

In another preferred embodiment, thermodilution computer 16 is coupled to an infusion pump 52 (shown in phantom in FIG. 1) or other automatic drug delivery system. When such an infusion pump is provided, thermal indicator 38 is automatically injected so that syringe 22 can be eliminated and operator intervention minimized.

Figure 2:
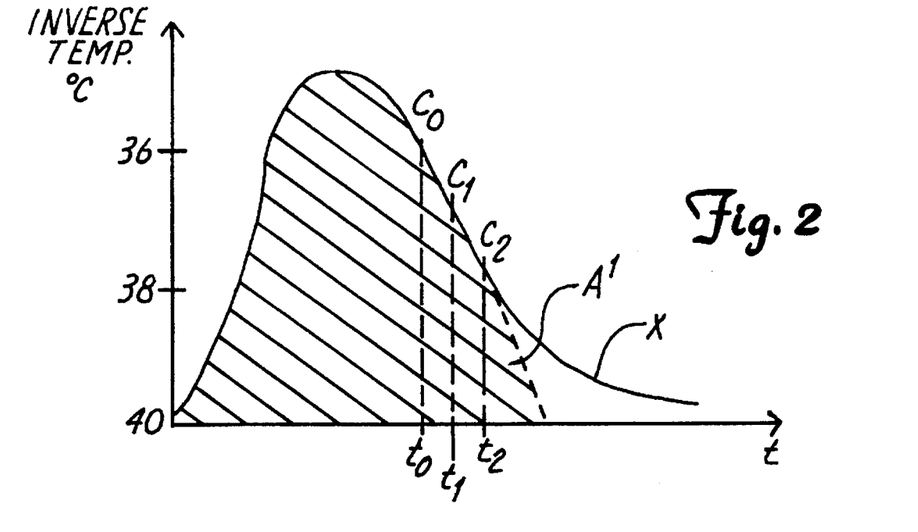
FIG. 2 illustrates a time-temperature curve obtained using a system according to the present invention.

FIG. 2 shows a time-temperature curve A generated by thermodilution computer 16 based upon the readings received from thermistors 32 and 36. Curve A shows that, as soon as thermal indicator 38 reaches thermistor 32 there is a sharp decrease in the temperature of the blood flowing past thermistor 32. This is indicated by a sharp increase in curve A along the inverse temperature axis of the graph in FIG. 2. Then, as the blood containing the thermal indicator 38 is pumped through pulmonary artery 42, and non-cooled recirculated blood enters pulmonary artery 42, the temperature of the blood begins to increase (thus the decline of curve A).

Curve A contains a tail portion X which shows that the blood continues, for some time, to have a temperature which is lower than the baseline temperature which existed before injection of thermal indicator 38. However, this is due to recirculated blood, which contains thermal indicator 38, re-entering the heart and being pumped again through pulmonary artery 42. Since the area under curve X represents recirculated blood and does not accurately represent the amount of blood initially pumped from right ventricle 50, it should be discarded in determining cardiac output. The area under curve X can be discarded by extrapolating curve A to the baseline temperature along an exponential downslope indicated by dashed line A'. Computer 16 performs the extrapolation and integrates to determine the shaded area under curves A and A'. Calculation of the exponential decay along curve A' can be determined using conventional methods which utilize two points on the exponential downslope according to the equation $C=C_0 e^{-kt}$ where:

$$k = \frac{2.3 \log_{10}(C_1/C_0)}{t_2 - t_1} \quad \text{Eq. 1}$$

$C_0$ is chosen as curve A begins an exponential downslope which is typically at approximately 80% peak value. $C_1$ is preferably chosen at approximately 65% peak value, and $C_2$ is chosen at approximately 50% peak value. Once the area under curves A and A' are determined, the cardiac output can be calculated according to the equation:

$$CO = \frac{\rho_i C_i (T_b - T_i) V_i (60)}{\rho_b C_b \times \int_0^\infty \Delta T_b(t) dt} \quad \text{Eq. 2}$$

where:
CO=cardiac output;
$V_i$=volume of thermal indicator 38 (ml) injected;
$\rho_i$=specific gravity of thermal indicator 38;
$\rho_b$=specific gravity of blood;
$C_i$=specific heat of thermal indicator 38;
$C_b$=specific heat of blood;
$T_b$=initial temperature of blood (° C.) measured by thermistor 32;
$T_i$=initial temperature of thermal indicator 38 measured by thermistor 36;
60 =60 seconds/minute; and $$\int_0^\infty \Delta T_b(t) dt = \text{area under curves } A \text{ and } A' \text{ in °C. sec.}$$

When 10 ml of 5% dextrose in water are injected as thermal indicator 38, then:

$$\frac{\rho_i C_i}{\rho_b C_b} = 1.08.$$

when cooled blood is used, then:

$$\frac{\rho_i C_i}{\rho_b C_b} = 1.00.$$

Once thermodilution computer 16 determines the cardiac output from the cardiac output test, the value is provided to printer 18 for printing, or displayed at display 20, or both. Significantly, the initial temperature of thermal indicator 38 ($T_i$) is measured by thermistor 36 just prior to its injection into heart 12. Therefore, there is no need for an estimated correction factor to be introduced into Equation 2 to compensate for warming of thermal indicator 33 during the injection process. Rather, the present invention eliminates this major source of error in determining cardiac output which existed in prior systems.

Also, since the signal from thermistor 36 substantially indicates the moment at which thermal indicator 38 is injected through port 34, and since thermodilution computer 16 begins the cardiac output test upon receiving the signal from thermistor 36, the physician does not need to actuate any switch or other input device to trigger thermodilution computer 16 to begin the cardiac output test. This also eliminates sources of error which were found in prior systems.

Further, the results of the initial cardiac output test need not be discarded as with prior systems. Since thermistor 36 measures the temperature of thermal indicator 38 as it is being injected into heart 12, there is no need to use a correction factor, so cooling of catheter 14 during the initial cardiac output test has no affect on subsequent calculations.

Figure 3:
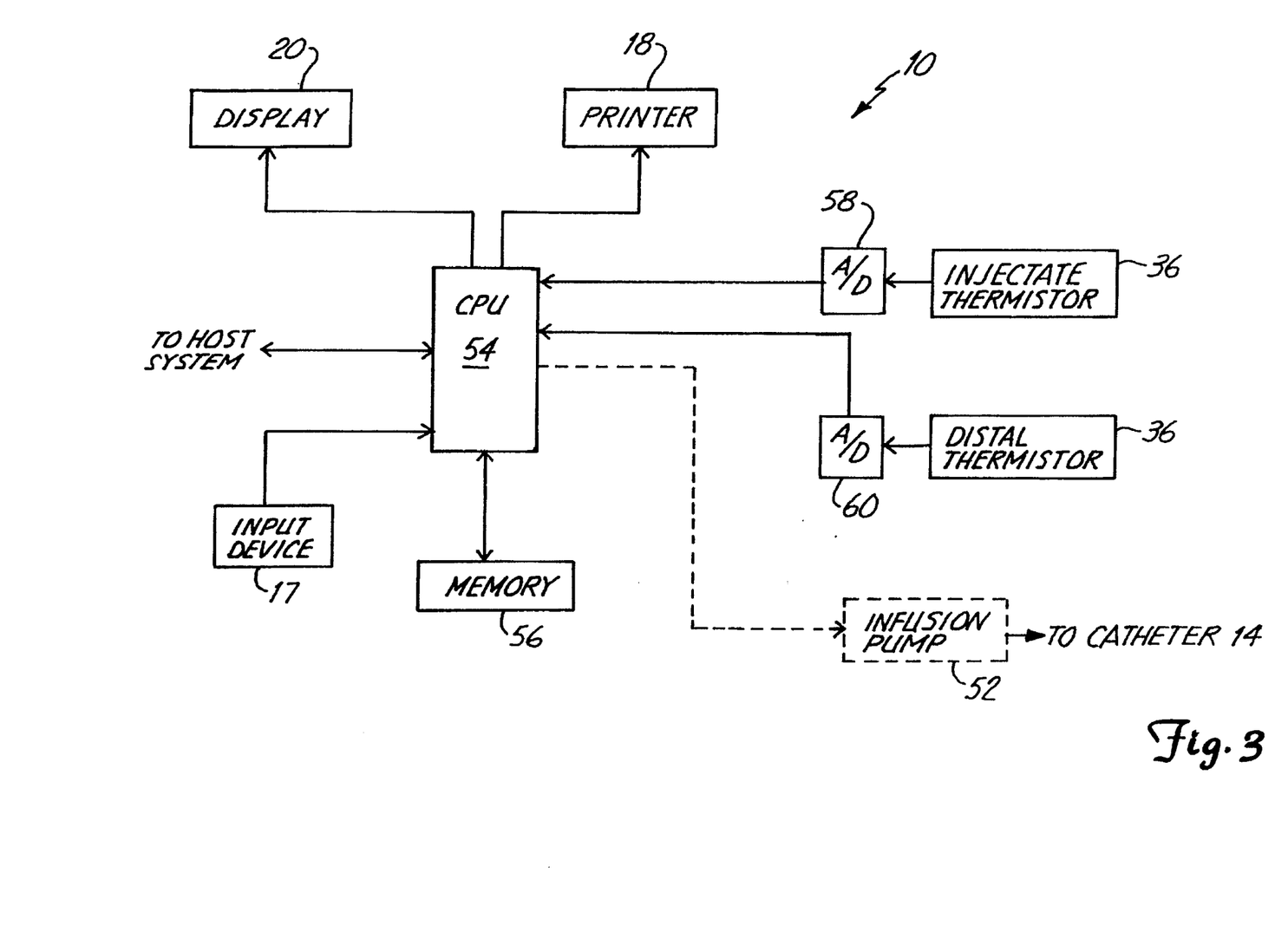
FIG. 3 is a block diagram of a control system according to the present invention.

FIG. 3 is a block diagram showing system 10 in greater detail. Similar items are similarly numbered to those shown in FIG. 1. FIG. 3 shows that system 10 includes a central processing unit 54, memory 56, and analog-to-digital (A/D) converters 58 and 60. A/D converters 58 and 60 are coupled to thermistors 36 and 32, respectively. The signals from thermistors 36 and 32 are converted to digital signals by A/D converters 58 and 60 for use by CPU 54. It should also be noted that other customary signal conditioning, such as amplification and linearization, are also provided to the signals from thermistors 32 and 36, where desired.

CPU 54 is preferably a digital computer or other suitable controller having appropriate timing means, such as a crystal oscillator, for synchronizing various components of thermodilution computer 16.

During a cardiac output test CPU 54 obtains data points for the time-temperature curve shown in FIG. 2. These data points are stored in memory 56. The data points are preferably associated in memory 56 with the other parameters input by the operator, such as patient identification, date, time, and other patient parameters.

In the preferred embodiment, a number of cardiac output tests are performed over a period of time. The results of the time-temperature curves obtained for these cardiac output tests are then averaged by CPU 54 and the average time-temperature curve is stored in memory 56. Such averaging can be performed using any number of known techniques. averaging a number of tests, minor aberrations in the cardiac output curve due to physiological factors are averaged out of the cardiac output value and the average time-temperature curve obtained. Thus, averaging provides a more accurate representation of the cardiac output of the patient.

In addition, the physician can track patient progress by obtaining a number of averages over a long period. For example, results of a plurality of tests performed within a time period of several minutes are averaged and stored in memory 56. An hour later, the results of another plurality of tests performed in a short time period are averaged and stored in memory 56. By obtaining a plurality of averages wherein the averages were determined by cardiac output tests performed within a relatively short time (e.g., within minutes), and spaced by a larger time period (e.g., an hour), the physician can accurately monitor progress of the patient. Each of the curves and cardiac output values can be displayed, either superimposed over one another, or displayed sequentially, by display 20. In addition, the curves and values can also be printed at printer 18.

Memory 56 is preferably large enough to store a number of average cardiac output values and time-temperature curves for each of a number of patients.

It should be noted that, in the preferred embodiment, CPU 54 is provided for being coupled to a host system, or another thermodilution computer 16. Suitable coupling methods include an RS 232 serial port, or a suitable parallel port.

It should also be noted that thermistors 32 and 36 typically do not provide an output which is linearly related to temperature. Thus, known logarithmic equations are used in converting the signals from thermistors 32 and 36 to temperature values. Alternatively, extrapolations are used from a look-up table stored in memory 56.

Figure 4:
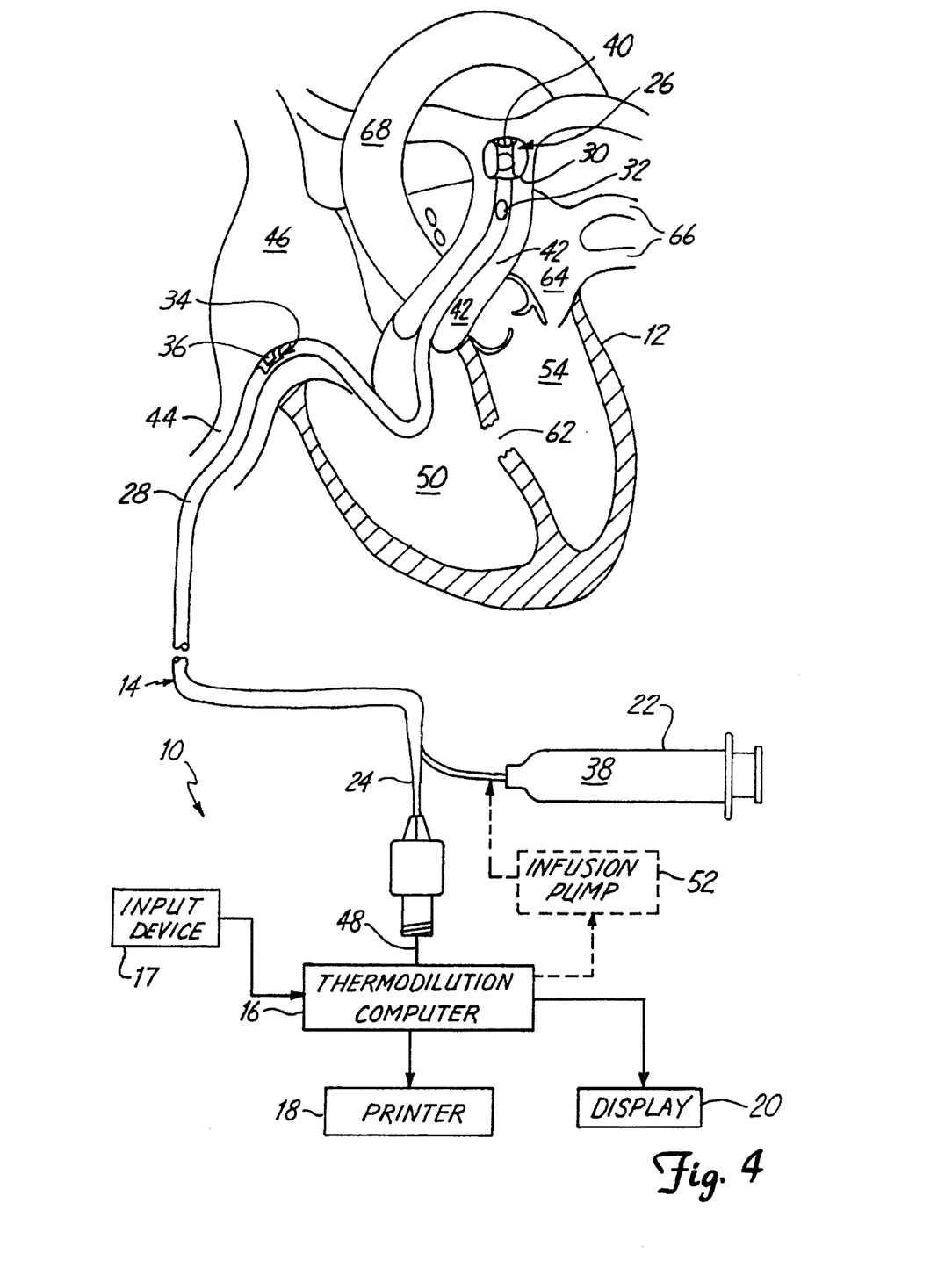
FIG. 4 illustrates the present invention in use with a patient having a septal defect.

FIG. 4 shows system 10 used in a similar manner to that shown in FIG. 1 except that heart 12 has a septal defect 62. Septal defect 62 provides fluid communication between right ventricle 50 and left ventricle 64 of heart 12.

Defect 62 undesirably affects normal blood flow. Normally, systemic blood flow returns to right atrium 46, is pumped into right ventricle 50, through pulmonary artery 42, to the lungs. The blood flow through pulmonary artery 42 is referred to as pulmonary blood flow. From the lungs, the blood flow re-enters left atrium 64 of heart 12 through pulmonary veins 66. This return flow is then pumped from left atrium 64 to left ventricle 54, through aorta 68 to the rest of the bodily tissues. The flow entering aorta 68 is referred to as systemic blood flow.

However, the resistance to systemic blood flow through aorta 68 is significantly higher than the resistance to pulmonary flow through pulmonary artery 42. Thus, during operation of heart 12 which includes defect 62, shunt flow occurs across defect 62 between left ventricle 54 and right ventricle 50. This causes blood which has just returned from the lungs to be pumped back through pulmonary artery 42 rather than through aorta 68.

Shunt flow across defect 62, after an injection of thermal indicator 38 has taken place, is significantly cooler than returned systemic flow since the circulation of the shunt flow has only been to the lungs and back, rather than through the entire system. Thus, thermistor 32 does not provide a typical time-temperature curve such as that shown in FIG. 2.

Figure 5:
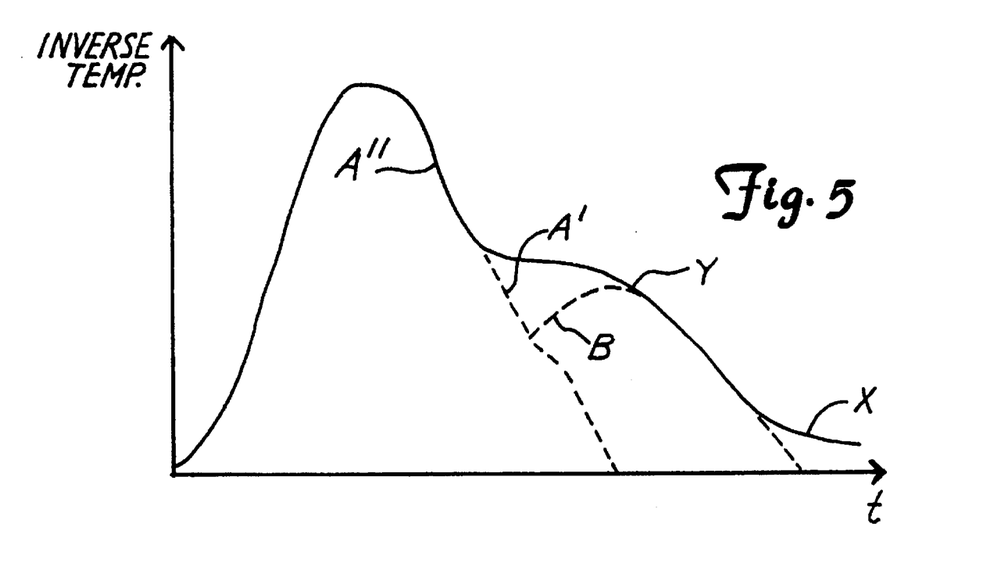
FIG. 5 is a graph of a time-temperature curve obtained using the system shown in FIG. 4.

Rather, the time-temperature curve provided by thermistor 32 is indicated by the curve shown in FIG. 5. The curve has a first portion A" similar to portion A in FIG. 2. However, the curve in FIG. 5 also has a significant deflection Y which is caused by the shunt flow through defect 62. The shunt flow, by itself, is represented by curve B shown in phantom in FIG. 5. Curve A', as in FIG. 1, represents the exponential downslope extrapolation of curve A" to the baseline temperature. The area under curves A" and A' can be obtained using substantially the same method as that described with respect to FIG. 2. In addition, by taking the total area under the curve shown in FIG. 5 minus the area under curves A" and A', and minus the area due to recirculation flow under curve X, the area under curve B (caused by shunt flow) can be determined using known techniques. Letting the area under curves A" and A' equal $A_p$ (representing pulmonary flow) and letting the area under curve B equal B, then the ratio of pulmonary blood flow ($Q_p$) to systemic blood flow ($Q_s$) can be determined by the known formula:

$$\frac{Q_p}{Q_s} = \frac{A_p}{A_p - B} \qquad \text{Eq. 4}$$

Thus, the shunt quantitation value corresponding to defect 62 can be determined by CPU 54 and stored along with other relevant data in memory 56 shown in FIG. 3.

Figure 6:
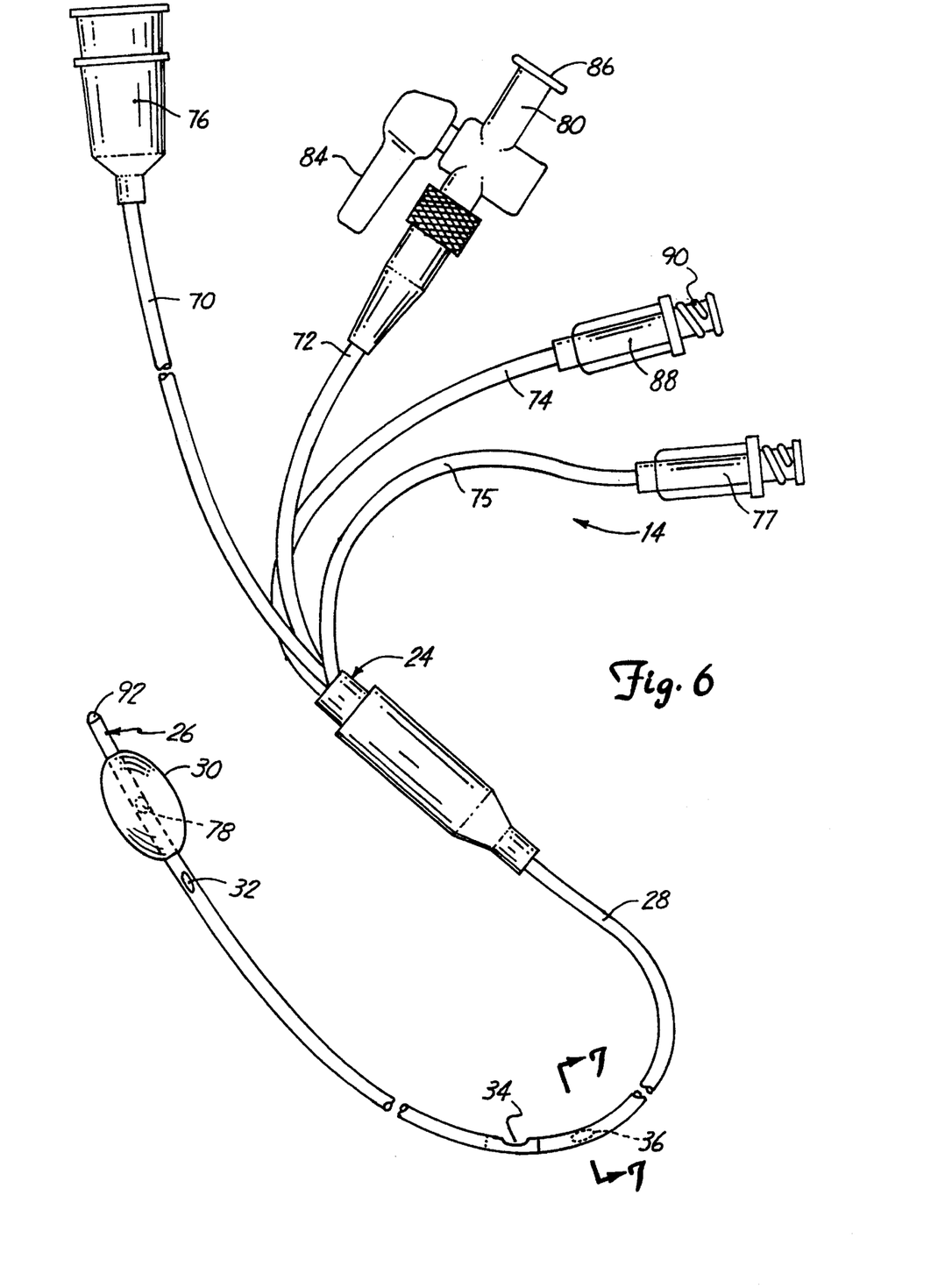
FIG. 6 is a thermodilution catheter according to the present invention.
Figure 7:
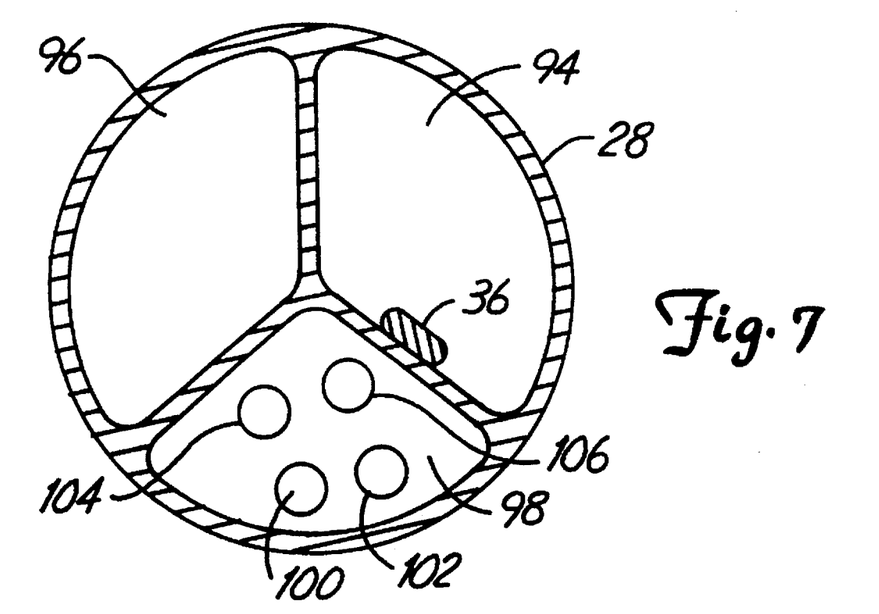
FIG. 7 is a cross-sectional view taken along section lines 7—7 in FIG. 6.

FIG. 6 and 7 show catheter 14 according to the present invention in more detail. Similar items are similarly numbered to those shown in FIG. 1 and 4. Tube 28 is a three-lumen tube having an injectate lumen 94, a balloon lumen 96 and a conductor lumen 98. Lumens 94, 96, and 98 are connected to a plurality of single-lumen catheters (or cables) 70, 72, 74 and 75 by junction connector 76. Cable 70 connects conductor lumen 98 in tube 28 to electrical thermistor connector 76. Thermistor connector 76 provides electrical connection between thermistors 32 and 36 and thermodilution computer 16. Electrical conductors 100, 102, 104 and 106 run from thermistors 32 and 36, through conductor lumen 98 in tube 28, through cable 70 and to connector 76. Thermodilution computer 16 has a mating connector (not shown), which mates with connector 76 for receiving the thermistor signals provided by thermistors 32 and 36.

Conductor lumen 98 is provided so that electrical conductors 100, 102, 104 and 106, are shielded from other, fluid-carrying, lumens in tube 28 and from the body.

Lumen 98 in tube 28 also communicates with the interior of balloon 30 through an aperture 78 in tube 28 (shown in phantom in FIG. 6). The lumen 98 is connected to cable 72 which is, in turn, connected to balloon connector 80. In the preferred embodiment, balloon connector 80 is a pitcock-type valve connector with a manual actuator 84 and a proximal receiving end 86. Proximal receiving end 86 is preferably sized to receive a standard Leaur-lock type of connector for a syringe (not shown) sized to match the balloon volume 39, or other appropriate means for providing pressure to inflate balloon 30 when desired. Actuator 84 is positionable to provide communication between receiving end 86 and cable 72 or to preclude communication between receiving end 86 and cable 72.

Injectate lumen 94 provides fluid communication between injection port 34 and cable 74. Cable 74 is, in turn, coupled to a fluid connector 88. Fluid connector 88 has a threaded end 90 which is threadably connectable to a female end of syringe 22. Thus, syringe 22 is in fluid communication with injection port 34. Alternatively, connector 88 is provided to achieve fluid communication with infusion pump 52, shown in FIG. 1 and 4.

In one preferred embodiment, catheter 14 also has a blood pressure port 92 which provides pressure communication with lumen 96. Lumen 96 is connected to cable 75 which is, in turn, connected to blood pressure connector 77. In this way, the treating physician can monitor blood pressure through connector 77.

Thermistor 36 is located in injectate lumen 94 so that it communicates, fluidly, with thermal indicator 38 as thermal indicator 38 passes through injectate lumen 94. However, thermistor 36 is located approximately 1 cm proximal of port 34 in injectate lumen 94. When catheter 14 is inserted in the blood stream, there is inherently back pressure developed at injection port 34 which causes blood to enter a short distance into injection port 34. In order to obtain a true reading of the injection temperature of thermal indicator 38 before it mixes with any blood that has entered injection port 34, thermistor 36 is located a suitable distance proximal of port 34 so that is senses the temperature of thermal indicator 38 before any mixing has occurred. This provides significant advantages over systems in which a thermistor is located in such a position that it senses the temperature of thermal indicator 38 after it has mixed with blood from the blood stream.

CONCLUSION

The present invention provides a cardiac output and shunt quantitation monitoring system which has significant advantages over prior systems. Thermistor 36 is located proximal of injection port 32. Thus, an accurate temperature measurement is obtained for thermal indicator 38 prior to its injection into the blood stream. This removes a significant source of error contained in prior systems. In addition, the signal from thermistor 36 is used to trigger the cardiac output test in thermodilution computer 16. This also removes a significant source of inaccuracies inherent in prior systems. Further, since thermistor 36 is located a sufficient distance proximal of port 34, thermistor 36 obtains a temperature reading for thermal indicator 38 before it mixes with any blood which may have entered port 34 due to back pressure in the blood stream.

Also, the present invention provides means for storing a number of time temperature curves obtained during cardiac output tests. These curves can be stored, and averaged, to obtain an accurate cardiac output measurement. In addition, a plurality of averages can be stored over time so that the treating physician can monitor the patient's progress for an extended period.

Finally, the present invention provides an efficient method of determining shunt quantitation ($Q_p/Q_s$). Thus, the present invention is far more versatile and useful than prior systems.

Although the present invention has been described with reference to preferred embodiments, workers skilled in the art will recognize that changes may be made in form and detail without departing from the spirit and scope of the invention.

What is claimed is:

1. A method of communicating cardiac output from a patient, comprising:

providing a catheter having a proximal end, a distal end, a lumen between the proximal end and the distal end of the catheter, and having an injection port communicating with the lumen;

placing a first temperature sensor in a blood vessel exiting a first heart chamber of the patient;

placing a second temperature sensor proximate the injection port;

performing a cardiac output test comprising:
   injecting injectate, having an injectate temperature, through the lumen into a second heart chamber of the patient:
   sensing the injectate temperature with the second temperature sensor;
   sensing blood temperature with the first temperature sensor as blood carrying the injectate passes through the blood vessel;
   storing a set of curve data representative of the sensed blood temperature as a function of time;

repeating the cardiac output test until a first plurality of sets of curve data are stored;

displaying at least one of the first plurality of sets of curve data; and wherein the second temperature sensor senses the injection of injectate and provides an initiation signal indicative of the injection of the injectate, and further comprising:
   triggering the step of performing the cardiac output test based on the initiation signal.

2. The method of claim 1 and further comprising:
   determining cardiac output based on the stored sets of curve data.

3. The method of claim 1 and further comprising:
   averaging the first plurality of sets of curve data to obtain a first average set of curve data.

4. The method of claim 3 wherein displaying comprises:
   displaying the first average set of curve data.

5. The method of claim 3 and further comprising:
   waiting for a delay time period after the first plurality of sets of curve data are stored; and
   repeating the cardiac output test until a second plurality of sets of curve data are stored.

6. The method of claim 5 and further comprising:
   averaging the second plurality of sets of curve data to obtain a second average set of curve data.

7. The method of claim 6 wherein displaying comprises:
   displaying the first and second average sets of curve data.

8. The method of claim 7 wherein displaying the first and second average set of curve data comprises:
   sequentially displaying the first and second average set of curve data.

9. The method of claim 6 and further comprising:
   comparing the first and second average sets of curve data to obtain a difference; and
   treating the patient based on the difference.

10. The method of claim 1 wherein placing a first temperature sensor in a blood vessel exiting a first heart chamber comprises:
    placing the first temperature sensor proximate to the distal end of the catheter; and placing the distal end of the catheter in the blood vessel.

11. The method of claim 1 wherein placing a second temperature sensor proximate the injection port comprises:

placing the second temperature sensor within the lumen proximal of the injection port.

12. The method of claim 1 wherein placing the distal end of the catheter in the blood vessel comprises:

placing the distal end of the catheter in a pulmonary artery of the patient so the injection port is proximate a right atrium of the patient.

13. The method of claim 1 and further comprising:

determining a ratio of pulmonary blood flow to systemic blood flow based on the first plurality of sets of curve data.

14. The method of claim 13 and further comprising:

displaying the ratio of pulmonary blood flow (Op) to systemic blood flow (Qs).

15. The method of claim 14 and further comprising:

treating the patient based on the ratio of Qp to (Qs).

16. An apparatus for communicating cardiac output from a patient, the apparatus comprising:

a catheter having a proximal end, a distal end, a lumen between the proximal end and the distal end of the catheter and an injection port communicating with the lumen;

a first temperature sensor at the distal end of the catheter communicating with an exterior of the catheter for sensing blood temperature and providing a blood temperature signal based on the blood temperature;

a second temperature sensor proximate the injection port of the catheter;

injection means, coupled to the catheter and communicating with the lumen, for injecting an injectate, having an injectate temperature, through the lumen and out the injection port, the second temperature sensor sensing the injectate temperature and providing an injectate temperature signal indicative of the injectate temperature;

controller means, coupled to the first temperature sensor and the second temperature sensor, for receiving the blood temperature signal and the injectate temperature signal from the first and second temperature sensors and for determining blood temperature, and injectate temperature;

storage means, coupled to the controller means, for storing a set of curve data representative of the blood temperature as a function of time;

display means, coupled to the controller, for displaying the set of curve data;

wherein the second temperature sensor is located in the lumen proximal of the injection port; and wherein the temperature sensor signal provided by the second temperature sensor triggers the controller means to begin obtaining the set of curve data.

17. The apparatus of claim 16 wherein the controller means includes:

means for determining a ratio of pulmonary blood flow to systemic blood flow based on the set of curve data obtained.

18. The apparatus of claim 16 wherein the controller means includes means for determining cardiac output based on the set of curve data and injectate temperature signal.

19. The apparatus of claim 16 wherein the controller means further comprises:

means for obtaining a plurality of sets of curve data and for averaging the plurality of sets of curve data to obtain a set of average curve data.

* * * * *